United States Patent [19]

Corfield et al.

[11] Patent Number: 4,558,124
[45] Date of Patent: Dec. 10, 1985

[54] PREPARATION OF CEPHALOSPORIN INTERMEDIATE COMPOUNDS

[75] Inventors: John R. Corfield, Runcorn; Andrew S. Miller, Marple, both of England

[73] Assignee: Lilly Industries Limited, London, England

[21] Appl. No.: 498,234

[22] Filed: May 26, 1983

[30] Foreign Application Priority Data

May 26, 1982 [GB] United Kingdom ............... 8215418

[51] Int. Cl.$^4$ ............... C07D 501/24; A61K 31/545
[52] U.S. Cl. ............................ 544/22; 544/16; 544/26; 260/245.2 R; 260/239 A; 260/239.1
[58] Field of Search ............ 260/245.2 R, 245.2 T; 424/270, 271; 544/16, 22, 21

[56] References Cited

U.S. PATENT DOCUMENTS

| | | | |
|---|---|---|---|
| 3,671,449 | 6/1972 | Jackson | 252/182 |
| 3,694,437 | 9/1972 | Jackson | 260/243 C |
| 4,075,337 | 2/1978 | Marx et al. | 424/246 |
| 4,346,219 | 8/1982 | Vladuchick | 544/28 |

FOREIGN PATENT DOCUMENTS 1594271  7/1981  United Kingdom ............... 499/46

OTHER PUBLICATIONS

S. Djuric et al., Silicon in Synthesis: Stabase Adducts—etc., *Tet. Letters*, 22, p. 1787, (1981).
R. D. G. Cooper et al., Structural Studies on Penicillin Derivatives, II, etc., *J. Amer. Chem. Soc.*, 91, p. 1528, (1969).
D. H. R. Barton et al., Stereoisomerism of Penicillin Sulfoxides, *J. Amer. Chem. Soc.*, 91, p. 1529, (1969).
W. Durckheimer et al., HR 109, A Highly Active Cephalosporin etc., *Recent Advances in the Chemistry of β-Lactam Antibiotics*, G. I. Gregory, Ed., Royal Society of Chemistry, London, 1981, pp. 48–49.
W. J. Wheeler et al., Bis–Trimethylsilylcefamandole: etc., *J. Antibiotics*, XXXIII, p. 72, (1980).

*Primary Examiner*—Nicholas S. Rizzo
*Attorney, Agent, or Firm*—Paul C. Steinhardt; Arthur R. Whale

[57] ABSTRACT

There is described a process for preparing a sulphoxide of the formula

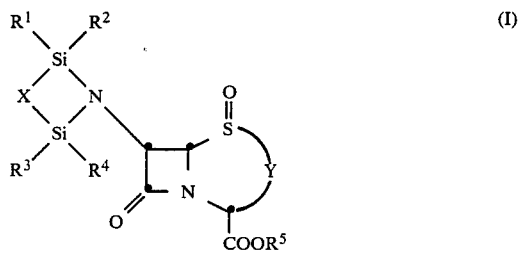

in which $R^1$, $R^2$, $R^3$ and $R^4$, taken individually, are alkyl, alkoxy or aryl groups, X is an alkylene group, $R^5$ is a carboxylic acid protecting group and Y is a linking group through one or two carbon atoms forming a penam or cephem nucleus, which comprises reacting a compound of formula

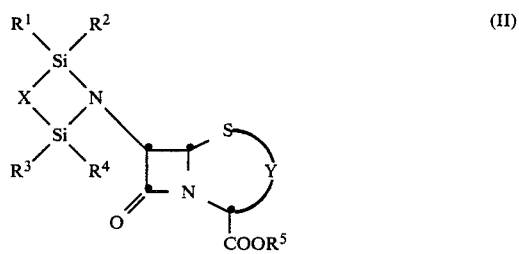

with an oxidizing agent.

α-Sulphoxide compounds of formula (I) are also provided as novel intermediates.

2 Claims, No Drawings

PREPARATION OF CEPHALOSPORIN INTERMEDIATE COMPOUNDS

This invention relates to a process for preparing penicillin and cephalosporin compounds and to novel intermediates used in the process.

The importance of certain penicillin α-sulphoxides as intermediates in the preparation of cephalosporin compounds has been described in British Pat. No. 2 003 475 where it is shown that the α-sulphoxide derivatives are preferred to the β-sulphoxide form in giving higher yields and involving the use of milder conditions.

In a paper in Tetrahedron Letters (Vol. 22, No. 19, pp 1787–1790, 1981). S. Djuric et al. disclose the preparation of a cyclic disilazine derivative of 6-aminopenicillanic acid, though this compound is not employed in the subsequent synthesis of further compounds.

We have now found that the silylation of certain penicillin or cephalosporin type nuclei assists in the preparation of α-sulphoxides in high yield.

Accordingly the invention provides a process for preparing a sulphoxide of the formula

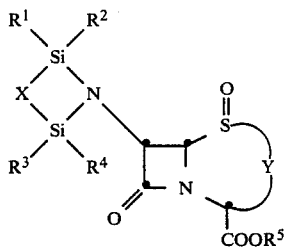

in which $R^1$, $R^2$, $R^3$ and $R^4$ are the same or different and are alkyl, alkoxy or aryl, X is alkylene, $R^5$ is a carboxylic acid protecting group and Y is a linking group through one or two carbon atoms forming a penam or cephem nucleus, which comprises reacting a compound of formula

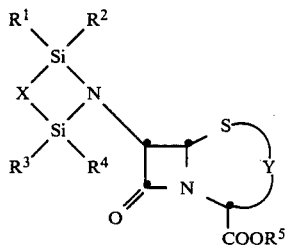

with an oxidising agent. Preferably the group Y is a group of the formula

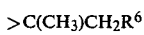

where $R^6$ is hydrogen, halo, methoxy, acetoxy, formyloxy, azido, nitro, cyano or phenylamino, or a group of the formula

where $R^7$ is methyl, halo, halomethyl or acetoxymethyl.

As described above, the oxidation reaction results in the production of predominantly or entirely the α-sulphoxide form and in general there is less then 10 percent of the β-sulphoxide present in the product, and the process may therefore be regarded as one for preparing the α-sulphoxide of formula (I).

Compounds of formula (I) are novel and are included as part of this invention. They are preferably prepared by the action of a peracid oxidising agent, in the presence of a base, since they are desilylated by the action of acid to give the corresponding free amino compound. The readiness with which this can be effected can represent a further advantage of the invention, the free amino compound being the necessary starting material for subsequent acylation to give active compounds or, in the case of penicillin type derivatives, for ring expansion reactions to provide cephalosporin compounds. Antibiotic cephalosporin and penicillin compounds prepared by the process of the invention or prepared from novel intermediates of the invention are included in the invention.

Alternatively the compound of formula (I) can be reacted directly with a selective acylating agent to give the desired acylated products. The intermediates of formula (II) are readily prepared from the corresponding free amino compound by reaction with a silylating agent of the formula

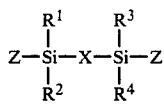

where Z is halogen. The compounds of formula (II) with the exception of the compound in which $R^1$, $R^2$, $R^3$ and $R^4$ are all methyl, X is —$(CH_2)_2$—, $R^5$ is methyl and Y is

are novel and are included as a further aspect of this invention.

Thus the invention also provides a process for producing a compound of the formula

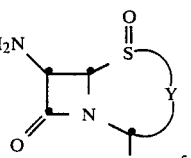

in which $R^5$ and Y have the above ascribed meanings, which comprises
(a) reacting a compound of the formula

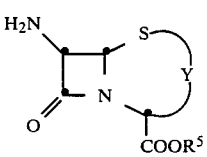

with a silylating reagent of formula

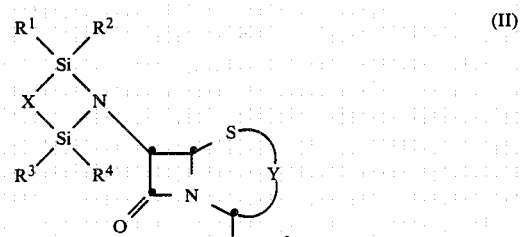

where $R^1$, $R^2$, $R^3$, $R^4$ and X have the meanings given above and Z is halogen, to give a compound of formula (II)

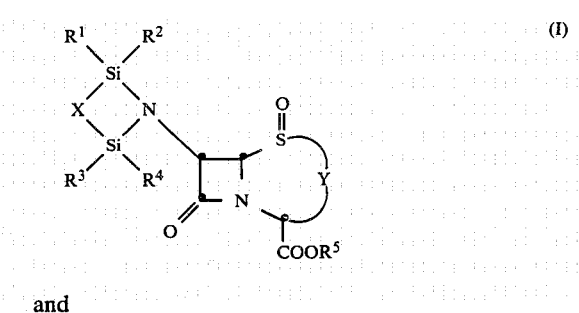

(b) reacting the compound of formula (II) with an oxidising agent to give a compound of formula

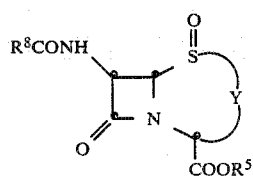

and (c) reacting the compound of formula (I) with acid. The compound of formula (IV) can then optionally be converted to its acylated products by employing an acylating agent of for example the formula $R^8COZ$ or an anhydride derivative of $R^8COOH$, where Z is halogen preferably chlorine, and $R^8$, together with the associated carbonyl group, is a carboxylic acid derived acyl group. Alternatively as stated above, the compound of formula (I) can be directly converted to its acylated product

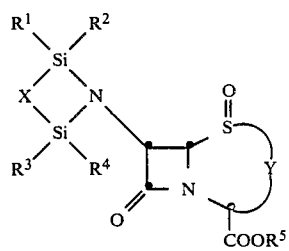

by reacting a compound of formula

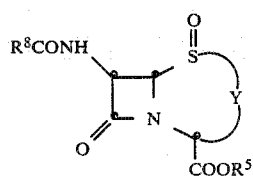

with an acylating agent of formula $R^8COZ$, where Z is halogen preferably chlorine, followed by treatment with water or an alcohol.

Conversion of the compound of formula (II) to that of formula (I) proceeds in the presence of an oxidising agent. The oxidising agent is preferably a peracid, especially peracetic acid, m-chloroperbenzoic acid or monoperphthalic acid. In view of the fact that the silyl protecting group is readily removed by acid, the reaction is performed in the presence of sufficient base to prevent loss of the side chain and is preferably conducted at a pH of from 7 to 13, more particularly in the range of 8 to 11. Convenient bases which may be employed with such acid oxidising agents are inorganic bases such as alkali metal or alkaline earth metal hydroxides, carbonates and bicarbonates and especially sodium hydroxide, sodium carbonate and sodium bicarbonate, or commercially available buffer solutions, or organic nitrogen bases such as for example triethylamine, dimethylaniline and pyridine. The reaction is also preferably carried out in the presence of an organic solvent for the compound of formula (I), and is most suitably conducted at a temperature of from $-10°$ C. to $30°$ C., such as from $0°$ C. to $5°$ C.

In the above formula (I), $R^1$, $R^2$, $R^3$ and $R^4$ can be alkyl and may be for example $C_{1-4}$ alkyl such as methyl, ethyl, n-propyl, isopropyl, n-butyl or t-butyl, the preferred value being methyl, or one or more of these groups may be alkoxy preferably $C_{1-4}$ alkoxy such as methoxy or ethoxy, or aryl such as for example phenyl or phenyl substituted with one or more, such as one to three, substituents selected, for example, from $C_{1-4}$ alkyl, nitro, halo, $C_{1-4}$ alkoxy. The group X is an alkylene chain preferably containing 1 to 5 carbon atoms and which can be for example $-(CH_2)_n-$ where n is an integer from 1 to 5. Preferred values of Y are

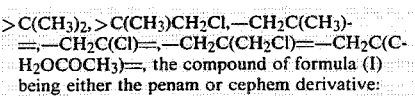

the compound of formula (I) being either the penam or cephem derivative:

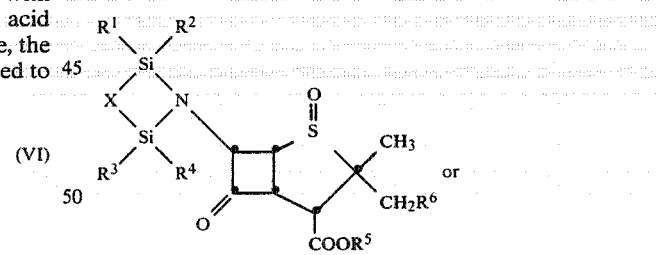

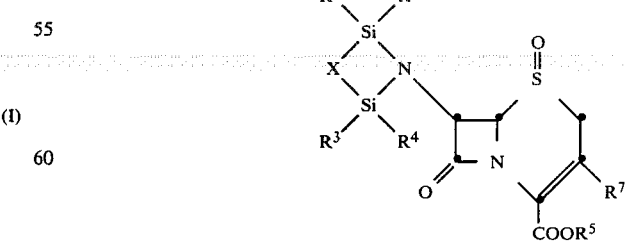

The group $R^5$ is a carboxylic acid protecting group. This term refers to the commonly used carboxylic acid protecting groups employed to block or protect the carboxylic acid functionality while reactions involving other functional sites of the compound are carried out. Such carboxy protecting groups are noted for their ease of cleavage by hydrolytic or by hydrogenolytic methods to the corresponding carboxylic acid. Examples of carboxylic acid ester protecting groups include methyl, tert-butyl, benzyl, 4-methoxybenzyl, $C_{2-6}$ alkanoyloxymethyl, 2-iodoethyl, p-nitrobenzyl, diphenylmethyl(benzhydryl), phenacyl, 4-halo-phenacyl, dimethylallyl, 2,2,2-trichloroethyl, tri($C_{1-3}$ alkyl)silyl, succinimidomethyl and like ester forming moieties. Other known carboxy protecting groups such as those described by T. W. Greene in "Protecting Groups in Organic Synthesis", Chapter 5, are also suitable. The nature of such ester forming groups is not critical although the use of the p-nitrobenzyl protecting group is often convenient.

The silylating reagent employed in the preparation of compounds of formula (II) is of the formula

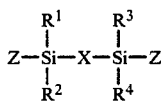

$R^1$, $R^2$, $R^3$ and $R^4$ are the same or different and are $C_{1-4}$ alkyl or aryl, being preferably methyl. The group X is preferably alkylene of the formula $—(CH_2)_n$ where n is an integer of from 1 to 5, and is most preferably 2, but can take other values as defined above. The group Z is halogen, preferably chlorine and examples of such silylating reagents are:

Cl(CH₃)₂Si—(CH₂)₂—Si(CH₃)₂Cl

Cl(CH₃)₂Si—(CH₂)₃—Si(CH₃)₂Cl

Cl(CH₃)₂Si—(CH₂)₄—Si(CH₃)₂Cl

Cl(CH₃)(Ph)Si—(CH₂)₂—Si(CH₃)(Ph)Cl

Cl(CH₃)(tBu)Si—(CH₂)₂—Si(CH₃)(tBu)Cl

Cl(CH₃)(OMe)Si—(CH₂)₂—Si(CH₃)(OMe)Cl

Cl(CH₃)(OEt)Si—(CH₂)₂—Si(CH₃)(OEt)Cl

The most preferred compound is

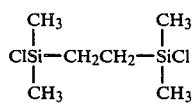

One example of a preferred process according to the invention is for the preparation of a compound of the formula

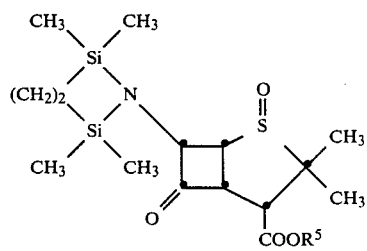

where $R^5$ is a carboxylic acid protecting group, which comprises reacting a compound of the formula

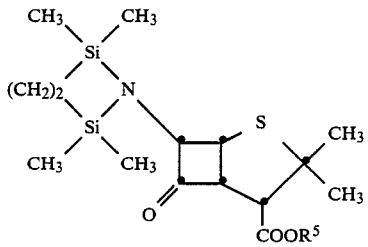

with a peracid oxidising agent in the presence of a base.

A further example of a preferred process according to the invention is for the preparation of a compound of the formula

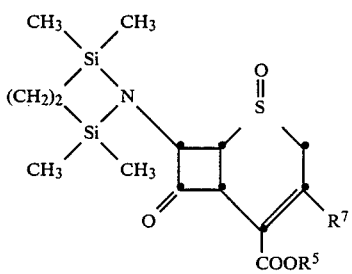

where $R^5$ is a carboxylic acid protecting group and $R^7$ is methyl or chloro, which comprises reacting a compound of formula

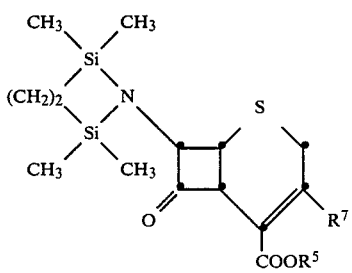

with a peracid oxidising agent in the presence of a base.

In order to convert the compound of formula (I) to that of formula (IV), by removal of the silyl group, conventional acid reagents may be employed preferably for example an acid such as hydrochloric acid or p-toluenesulphonic acid in an organic solvent for the reactants such as for example ethyl acetate or methylene chloride, the temperature employed being usually in the range of from $-10°$ to $50°$ C. The subsequent acylation of compounds of formula (IV) can be carried out in conventional manner employing a conventional acylating agent preferably in an organic solvent such as tetrahydrofuran, ether, acetonitrile or a chlorinated hydrocarbon such as dichloromethane, at a temperature of for example from $-10°$ to $50°$ C.

In the case of the direct acylation route (reaction of a compound of formula (I) with $R^8COZ$) the intermediate formed by the first stage of the acylation process is not isolated, the initial reaction being followed by reaction in situ with water or an alcohol such as for example ethanol at a temperature of from $-10°$ to $50°$ C. to liberate the acylated product.

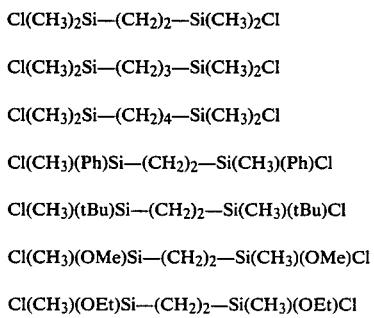

The carboxylic acid derived acyl group R⁸CO can be any of those groups conventionally utilised in the β-lactam art, the nature of which groups will be readily apparent to those skilled in this field of chemistry. Thus, for instance the R⁸ residue may be:

(a) hydrogen, $C_{1-3}$alkyl, halomethyl, cyanomethyl or 3-(2-chlorophenyl)-5-methylisoxazol-4-yl;

(b) benzyloxy, 4-nitrobenzyloxy, 2,2,2-trichloroethoxy, tert-butoxy, or 4-methoxybenzyloxy;

(c) the groups R" wherein R" is phenyl or phenyl substituted with 1 or 2 substituents independently selected from the group consisting of halo, protected hydroxy, nitro, cyano, trifluoromethyl, $C_{1-3}$alkyl, and $C_{1-4}$alkoxy;

(d) an arylalkyl group of the formula

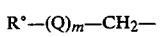

R°—(Q)ₘ—CH₂— wherein R° is R" as defined above, 2-thienyl, 3-thienyl, or 1,4-cyclohexyldienyl, m is 0 or 1, and Q is O or S subject to the limitation that when m is 1 R° is R";

(e) a substituted arylalkyl group of the formula

R°CH—
|
W wherein R° is as defined above and W is hydroxy, protected amino, or protected carboxy; or (f) a heteroarylmethyl group of the formula R⁴CH₂— wherein R⁴ is 2-furyl, 3-furyl, 2-thiazolyl, 5-isoxazolyl, or 5-tetrazolyl.

The residue R⁸ is preferably benzyl or phenoxymethyl (PhOCH₂—).

The utility of compounds of formula (IV) is well documented in the literature and has already been referred to. Acylation of the 6-amino group of the penanm derivative gives, for example, a 6-acylamido-2,2-dimethylpenam-3-carboxylic acid ester α-sulphoxide which on reaction with an N-chloro halogenating agent in the presence of an alkylene oxide as described for instance in British Pat. No. 2 003 375, gives the corresponding esters of a 3-methyl-2-(2-chlorosulphinyl-4-oxo-3-acylamido-1-azetidinyl)-3-butenoic acid of the general formula

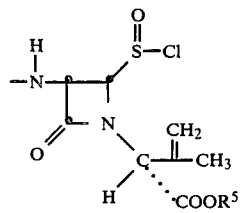

which are useful intermediates in the preparation of 7-acylamido-3-exomethylenecepham-4-carboxylic acid ester sulphoxides.

Acylation of both penam and cephem compounds of formula (IV), by well known techniques, can lead to the preparation of diacylated α-sulphoxide compounds, such as those disclosed in British Pat. No. 1 594 271 of the formula:

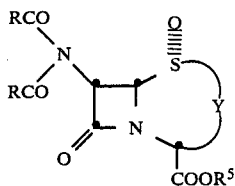

which are stated to have useful antibiotic properties.

The invention is illustrated by the following Examples.

EXAMPLE 1 p-Nitrobenzyl 6-(2,2,5,5-tetramethyl-1-aza-2,5-disilacyclopent-1-yl)penicillanate A solution of the p-toluenesulphonic acid salt of p-nitrobenzyl 6-aminopenicillanate (20.88 g) in methylene chloride (80 ml) was washed twice with saturated aqueous sodium bicarbonate (100 ml) and then brine (100 ml), dried with magnesium sulphate and the volume reduced to 40 ml by evaporation under reduced pressure. Triethylamine (13.92 ml) and a solution of 1,2-bis-(chlorodimethylsilyl)ethane (9.48 g) in methylene chloride (80 ml) were added and the resulting mixture refluxed for 15 hours under a nitrogen atmosphere. The reaction mixture was allowed to cool to room temperature and then washed with 8% aqueous sodium hydrogen phosphate solution (100 ml). The organic layer was separated, concentrated under reduced pressure to about 30 ml, and then diluted with isopropanol (200 ml). The remaining methylene chloride was evaporated under reduced pressure to crystallise the product. The reaction mixture was cooled to 0° C. for 2 hours and then the product isolated by filtration, washed with cold isopropanol and dried overnight in vacuo at room temperature to give the title compound as white crystals, nmr (CDCl₃) δ 0.15 (s, 12H), 0.72 (s, 4H), 1.40 (s, 3H), 1.64 (s, 3H), 4.27 (s, 1H), 4.72 (d, J=4 Hz, 1H), 5.15 (d, J=4 Hz, 1H), 5.16 (s, 2H), 7.3–8.2 (m, 4H).

The following compound was prepared in a similar manner:

Benzhydryl 6-(2,2,5,5-tetramethyl-1-aza-2,5-disilacyclopent-1-yl)-penicillanate, a foam, nmr (CDCl₃) δ 0.14 (s, 6H), 0.17 (s, 6H), 0.71 (s, 4H), 1.22 (s, 3H), 1.62 (s, 3H), 4.37 (s, 1H), 4.78 (d, J=4 Hz, 1H), 6.86 (s, 1H), 7.20 (s, 10H).

EXAMPLE 2 p-Nitrobenzyl 6-(2,2,5,5,-tetramethyl-1-aza-2,5-disilacyclopent-1-yl)penicillanate 1α-oxide To a stirred solution of p-nitrobenzyl 6-(2,2,5,5,-tetramethyl-1-aza-2,5-disilacyclopent-1-yl)penicillanate (2.61 g) in methylene chloride (50 ml) was added 0.5M aqueous sodium bicarbonate (15 ml) followed by m-chloroperbenzoic acid (1.11 g) over 20 minutes. After 30 minutes a second amount of m-chloroperbenzoic acid (0.1 g) was added, the reaction mixture was stirred for a further 20 minutes when the layers were separated. The organic layer was dried over magnesium sulphate and concentrated under reduced pressure. Di-isopropyl ether was slowly added to the residue to crystallise the product. The residual methylene chloride was evaporated under reduced pressure and then the reaction was kept overnight at 0° C. to complete the crystallisation. The product was filtered off, washed with di-isopropyl ether, and dried in vacuo at room temperature overnight to give the title compound as creamy-white crystals, nmr (CDCl$_3$) δ 0.17 (s, 6H), 0.22 (s, 6H), 0.78 (s, 4H), 1.20 (s, 3H), 1.63 (s, 3H), 4.23 (s, 1H), 4.40 (d, J=4 Hz, 1H), 4.85 (d, J=4 Hz, 1H), 5.21 (s, 2H), 7.40 (d, J=9 Hz, 2H), 8.07 (d, J=9 Hz, 2H).

The following compound was prepared in a similar manner:

Benzyhydryl 6-(2,2,5,5-tetramethyl-1-aza-2,5-disilacyclopent-1-yl)penicillanate 1α-oxide as a foam, nmr (CDCl$_3$) Δ 0.15 (s, 6H), 0.20 (s, 6H), 0.77 (s, 4H), 1.0 (s, 3H), 1.62 (s, 3H), 4.27 (s, 1H), 4.41 (d, J=4 Hz, 1H), 4.85 (d, J=4 Hz, 1H), 6.85 (s, 1H), 7.20 (s, 10H).

EXAMPLE 3 p-Nitrobenzyl 6-(2,2,5,5-tetramethyl-1-aza-2,5-disilacyclopent-1-yl)penicillanate 1α-oxide Peracetic acid (36%, 2.65 ml) was added dropwise over 5 minutes to a rapidly stirred mixture of p-nitrobenzyl 6-(2,2,5,5-tetramethyl-1-aza-2,5-disilacyclopent-1-yl)penicillanate (6.9 g) in methylene chloride (50 ml) and 0.5M aqueous sodium bicarbonate (125 ml) at 0°-5° C. The reaction mixture was stirred for 45 minutes at 0°-5° C. The organic layer was separated, washed with water and concentrated under reduced pressure. Di-isopropyl ether (about 120 ml) was slowly added to the residue to crystallise the product. The residual methylene chloride was evaporated under reduced pressure and then the reaction was kept overnight at 0° C. to complete the crystallisation. The product was filtered off, washed with di-isopropyl ether, and dried in vacuo at 40° C. overnight to give the title compound as pale cream crystals.

EXAMPLE 4 p-Nitrobenzyl 6-(2,2,5,5-tetramethyl-1-aza-2,5-disilacyclopent-1-yl)penicillanate 1α-oxide A solution of monoperphthalic acid (0.51 g) in diethyl ether (12 ml) was added dropwise over 5 minutes to a rapidly stirred mixture of 5% aqueous sodium bicarbonate (30 ml) and a solution of p-nitrobenzyl 6-(2,2,5,5-tetramethyl-1-aza-2,5-disilacyclopent-1-yl)penicillanate (1.24 g) in methylene chloride (10 ml) at 0°-5° C. The mixture was stirred for 30 minutes at 0°-5° C. The organic layer was separated, washed with brine, dried with magnesium sulphate, and concentrated by evaporation under reduced pressure. Di-isopropyl ether was added and the residual methylene chloride removed by evaporation in vacuo to crystallise the product. The product was filtered off, washed with di-isopropyl ether and dried in vacuo to give the title compound as pale cream crystals.

EXAMPLE 5 p-Nitrobenzyl 6-aminopenicillanate-1α-oxide

To a stirred solution of p-nitrobenzyl 6-(2,2,5,5-tetramethyl-1-aza-2,5-disilacyclopent-1-yl)penicillanate 1α-oxide (1.35 g) in ethyl acetate (10 ml) was added p-toluenesulphonic acid monohydrate (1.9 g) in ethyl acetate (20 ml). After 30 minutes the solvents were removed in vacuo to give a gum, from which the title compound was obtained as its tosylate salt by trituration with ether. $^1$H nmr (d$_6$ DMSO δ values) 1.22 (s, 3H), 1.60 (s, 3H), 3.30 (s, 3H), 4.67 (s, 1H), 4.78 (d, J=4 Hz, 1H), 5.17 (d, J=4 Hz, 1H), 5.35 (s, 2H), 7.07 (d, J=8 Hz, 2H), 7.53 (d, J=8 Hz, 2H), 7.67 (d, J=8 Hz, 2H), 8.17 (d, J=8 Hz, 2H).

EXAMPLE 6 p-Nitrobenzyl 6-phenoxyacetamidopenicillanate 1α-oxide

To a stirred solution of p-nitrobenzyl 6-aminopenicillanate-1α-oxide (1.85 g) in methylene chloride (50 ml) was added 0.5M aqueous sodium bicarbonate solution (20 ml) followed by phenoxyacetyl chloride (0.83 ml), and the stirring continued for 60 minutes. The organic phase was separated off, dried over magnesium sulphate and stripped of solvents in vacuo to give the title compound. $^1$H nmr (CDCl$_3$) Δ 1.25 (s, 3H), 1.63 (s, 3H), 4.5 (s, 3H), 4.73 (d, J=4 Hz, 1H), 5.27 (s, 2H), 5.37 (d, J=4 Hz and 8 Hz), 6.7–7.3 (m, 5H), 7.47 (d, J=8 Hz, 2H), 8.13 (d, J=8 Hz, 2H).

EXAMPLE 7 p-Nitrobenzyl 6-phenoxyacetamidopenicillanate 1α-oxide

Phenoxyacetyl chloride (1.49 ml) was added dropwise to a stirred solution of p-nitrobenzyl 6(2,2,5,5-tetramethyl-1-aza-2,4-disilacyclopent-1-yl)penicillanate 1α-oxide (5.0 g) in tetrahydrofuran (75 ml) at room temperature. After stirring for one hour at room temperature, the reaction mixture was washed with aqueous sodium hydrogen carbonate and then with water, dried with magnesium sulphate and evaporated in vacuo. The product was crystallised from isopropanol, collected by filtration, washed with isopropanol and dried in vacuo to give the title compound. nmr (CDCl$_3$) δ 1.20 (s, 3H), 1.56 (s, 3H), 3.64 (s, 2H), 4.45 (s, 1H), 4.63 (d, J=4 Hz, 1H), 5.0–5.3 (m, 3H), 7.18 (s, 5H), 7.3–8.2 (m, 4H).

EXAMPLE 8

Benzhydryl 6-(phenoxyacetamido)penicillanate 1α-oxide

A mixture of p-toluenesulphonic acid monohydrate (1.34 g) and benzhydryl 6-(2,2,5,5-tetramethyl-1-aza-2,5-disilacyclopent-1-yl)penicillanate 1α-oxide (3.60 g) in ethyl acetate (25 ml) was stirred for 1.5 hours at room temperature. The solvent was evaporated under reduced pressure and the residue crystallised from diethyl ether to give yellow crystals of the p-toluenesulphonic acid salt of benzhydryl 6-aminopenicillanate 1α-oxide (2.03 g). A solution of this tosylate in methylene chloride (25 ml) was washed twice with saturated aqueous sodium bicarbonate (25 ml) and then brine (25 ml), and then stirred rapidly for 3 hours at room temperature with phenoxyacetyl chloride (0.46 ml) and saturated aqueous sodium bicarbonate (25 ml). The organic layer was separated, washed with saturated aqueous sodium bicarbonate, dried with magnesium sulphate, and evaporated under reduced pressure to give the title compound as a foam, nmr (CDCl$_3$) δ 1.03 (s, 3H), 1.60 (s, 3H), 4.46 (s, 1H), 4.64 (d, J=4 Hz, 1H), 5.42 (dd, J=4 and 8 Hz, 1H), 6.78 (d, J=4 Hz, 1H), 6.84 (s, 1H), 7.16 (s, 10H).

EXAMPLE 9 p-Nitrobenzyl 6-(2,5-dibutyl-2,5-dimethyl-1-aza-2,4-disilacyclopent-1-yl)penicillanate A solution of the p-toluenesulphonic acid salt of p-nitrobenzyl 6-aminopenicillanate (2.61 g) in CH$_2$Cl$_2$ (50 ml) was washed twice with saturated aqueous sodium bicarbonate and then with brine, dried with sodium sulphate and evaporated in vacuo. To a solution of the residual amine in acetonitrile (50 ml) was added 1,2-bis(chlorodimethylsilyl)ethane (1.65 g) and triethylamine (1.55 ml) and the mixture was heated at reflux for 3.5 hours, allowed to cool to room temperature, and then washed with aqueous 8% sodium hydrogen phosphate solution. The organic solution was evaporated and the residue chromatographed on alumina with methylene chloride-ethyl acetate 3:1 as eluent to give the title compound as a foam, nmr (CDCl$_3$) δ 0.10 (s, 6H), 0.22 (s, 6H), 0.6–1.5 (m, 22H), 1.73 (s, 3H), 4.33 (s, 1H), 4.83 (d, J=4 Hz, 1H), 5.22 (d, J=4 Hz, 1H), 5.24 (s, 2H), 7.27–8.16 (m, 4H).

EXAMPLE 10 p-Nitrobenzyl 6-(penoxyacetamido)penicillanate 1α-oxide

To a stirred solution of p-nitrobenzyl 6-(2,5-dibutyl-2,5-dimethyl-1-aza-2,5-disilacyclopent-1-yl)penicillanate (0.5 mmol) at 0° C. was added 0.5M aqueous sodium bicarbonate (1.5 ml) followed by portionwise addition of m-chloroperbenzoic acid (0.11 g) over 5 minutes. The reaction mixture was stirred and allowed to warm up to room temperature over 2 hours. The organic solution was separated and evaporated under reduced pressure. The residual 1α-sulphoxide derivative was dissolved in acetone (5 ml) and then stirred with 1N hydrochloric acid (0.55 ml) for 30 minutes. The resulting mixture was diluted with methylene chloride and then the organic layer was separated, washed with water and then saturated aqueous sodium bicarbonate, dried with sodium sulphate and evaporated under reduced pressure to give p-nitrobenzyl 6-aminopenicillanate 1α-oxide.

A solution of this amine in methylene chloride (5 ml) was stirred overnight with a saturated aqueous sodium bicarbonate solution (5 ml) and phenoxyacetyl chloride (0.07 ml). The organic layer was separated, washed with water, dried with magnesium sulphate, and evaporated under reduced pressure to give the title compound.

EXAMPLE 11 p-Nitrobenzyl 7-(2,2,5,5-tetramethyl-1-aza-2,5-disilacyclopent-1-yl)desacetoxycephalosporanate To a stirred solution of p-nitrobenzyl 7-aminodesacetoxycephalosphoranate (3.5 g) in methylene chloride (15 ml) under nitrogen was added triethylamine (3.2 ml) followed by a solution of 1,2-bis(chlorodimethylsilyl)ethane (2.37 g) in methylene chloride (20 ml). The resulting mixture was stirred at reflux for 16 hours, allowed to cool to room temperature and then washed once with aqueous 8% sodium hydrogen phosphate solution (30 ml). The organic solution was concentrated in vacuo to about 10 ml and isopropanol (30 ml) added. The remaining methylene chloride was removed in vacuo and the reaction mixture was cooled to 0° C. for two hours. The product was filtered off, washed with cold isopropanol and dried overnight in vacuo to give the title compound, nmr (CDCl$_3$) δ 0.19 (s, 12H), 0.75 (s, 4H), 2.10 (s, 3H), 3.15+3.60 (ABq, J=18 Hz, 2H), 4.73 (d, J=4 Hz, 1H), 4.93 (d, J=4 Hz, 1H), 5.30 (s, 2H), 7.53 (d, J=8 Hz, 2H), 8.15 (d, J=8 Hz, 2H).

The following compounds were prepared in a similar manner:

Benzhydryl 7-(2,2,5,5-tetramethyl-1-aza-2,5-disilacyclopent-1-yl)-desacetoxycephalosporanate, a pale yellow foam, nmr (CDCl$_3$) δ 0.16 (s, 12H), 0.73 (s, 4H), 1.69 (s)+1.86 (s) (3H), 2.90+3.33 (ABq, J=18 Hz, 2H), 4.5–5.0 (m, 2H), 6.73 (s)+6.80 (s) (1H), 7.12 (s, 10H).

p-Methoxybenzyl 7-(2,2,5,5-tetramethyl-1-aza-2,5-disilacyclopent-1-yl)desacetoxycephalosporanate, a gum, nmr (CDCl$_3$) δ 0.16 (s, 12H), 0.73 (s, 4H), 1.73 (s)+2.0 (s) (3H), 2.98+3.43 (ABq, J=18 Hz, 2H), 3.36 (s, 3H), 4.5–5.3 (m, 4H), 6.5–7.3 (m, 4H).

2,2,2-Trichloroethyl 7-(2,2,5,5-tetramethyl-1-aza-2,5-disilacyclopent-1-yl)desacetoxycephalosporanate, a gum, nmr (CDCl$_3$) δ 0.17 (s, 12H), 0.75 (s, 4H), 1.92 (s)+2.11 (s) (3H), 3.12+3.55 (ABq, J=18 Hz, 2H), 4.5–5.2 (m, 4H).

EXAMPLE 12 p-Nitrobenzyl 7-(2,2,5,5-tetramethyl-1-aza-2,5-disilacyclopent-1-yl)desacetoxycephalosporanate 1α-oxide Peracetic acid (36%, 0.88 ml) was added dropwise over 5 minutes to a rapidly stirred mixture of p-nitrobenzyl 7-(2,2,5,5-tetramethyl-1-aza-2,5-disilacyclopent-1-yl)desacetoxycephalosporanate (2.4 g) in methylene chloride (10 ml) and 0.5M aqueous sodium bicarbonate (20 ml) at 0°–5° C. The reaction mixture was stirred for 45 minutes at 0°–5° C. The organic layer was separated, washed with water, dried with magnesium sulphate, and evaporated in vacuo to give the title compound as a white foam, nmr (CDCl$_3$ δ 0.18 (s, 6H), 0.25 (s, 6H), 0.78 (s, 4H), 2.10 (s, 3H), 3.35+3.93 (ABq, J=18 Hz, 2H), 4.35 (d, J=4 Hz, 1H), 5.05 (d, J=4 Hz, 1H), 5.25 (s, 2H), 7.43 (d, J=8 Hz, 2H), 8.07 (d, J=4 Hz, 2H).

The following compounds were prepared in a similar manner:

Benzhydryl 7-(2,2,5,5-tetramethyl-1-aza-2,5-disilacyclopent-1-yl)-desacetoxycephalosporanate 1α-oxide, a wite solid, nmr (CDCl$_3$) δ 0.13 (s, 6H), 0.23 (s, 6H), 0.78 (s, 4H), 1.75 (s)+1.93 (s) (3H), 3.23+3.78 (ABq, J=17 Hz, 2H), 4.27–5.04 (m, 2H), 6.80 (s)+6.83 (s) (1H), 7.17 (s, 10H).

p-Methoxybenzyl 7-(2,2,5,5-tetramethyl-1-aza-2,5-disilacyclopent-1-yl)desacetoxycephalosporanate 1α-oxide, a yellow foam, nmr (CDCl$_3$) δ 0.2 (s, 12H), 0.78 (s, 4H), 1.82 (s)+1.99 (s) (3H), 3.22+3.80 (ABq, J=18 Hz, 2H), 3.68 (s, 3H), 4.23–4.48 (m, 1H), 4.8–5.2 (m, 3H), 6.5–7.3 (m, 4H).

2,2,2-Trichloroethyl 7-(2,2,5,5-tetramethyl-1-aza-2,5-disilacyclopent-1-yl)desacetoxycephalosporanate 1α-oxide, a yellow foam, nmr (CDCl$_3$) δ 0.18 (s, 6H), 0.26 (s, 6H), 0.81 (s, 4H), 2.02 (s)+2.15 (s) (3H), 3.35+3.92 (ABq, J=18 Hz, 2H), 4.3–5.2 (m, 4H).

EXAMPLE 13 p-Nitrobenzyl 7-aminodesacetoxycephalosporanate 1α-oxide p-Nitrobenzyl 7-(2,2,5,5-tetramethyl-1-aza-2,5-disilacyclopent-1-yl)desacetoxycephalosporanate 1α-oxide (2.0 g) in methylene chloride (15 ml) was stirred with 5% hydrochloric acid (15 ml) for 30 minutes. The resulting precipitate was filtered off and dried overnight in vacuo at 40° C. to give the hydrochloride salt of the title compound, nmr (d$_6$-DMSO) δ 2.23 (s, 2H), 3.82+4.44 (ABq, J=24 Hz, 2H), 4.67 (d, J=6 Hz, 2H), 5.28 (d, J=6 Hz, 2H), 5.33 (s, 2H), 7.53 (d, J=12 Hz, 2H), 8.03 (d, J=12 Hz, 2H).

The following compounds were prepared in a similar manner:

Benzhydryl 7-aminodesacetoxycephalosporanate 1α-oxide, pale yellow crystals, nmr (d$_6$-DMSO) δ 1.98 (s, 3H), 2.97 (br. s, 2H), 3.55+4.07 (ABq, J=17 Hz, 2H), 4.58 (d, J=4 Hz, 1H), 4.87 (d, J=4 Hz, 1H), 6.77 (s, 1H), 7.22 (s, 10H).

p-Methoxybenzyl 7-aminodesacetoxycephalosporanate 1α-oxide, a pale yellow solid, nmr (CDCl$_3$) δ 2.01 (s, 3H), 2.50 (br. s, 2H), 3.36+3.83 (ABq, J=18 Hz, 2H), 4.42 (d, J=3 Hz, 1H), 4.80 (d, J=3 Hz, 1H), 5.1 (s, 2H), 6.6-7.3 (m, 4H).

EXAMPLE 14 p-Nitrobenzyl 7-phenoxyacetamidodesacetoxycephalosporanate 1α-oxide

Phenoxyacetyl chloride (0.3 ml) was added dropwise to a stirred solution of p-nitrobenzyl 7-(2,2,5,5-tetramethyl-1-aza-2,5-disilacyclopent-1-yl)desacetoxycephalosporanate 1α-oxide (1.0 g) in tetrahydrofuran (30 ml) at room temperature. After stirring for one hour at room temperature, the reaction mixture was washed with aqueous sodium hydrogen carbonate and then with water, dried with magnesium sulphate and evaporated in vacuo. The product was crystallised from isopropanol, collected by filtration, washed with isopropanol and dried in vacuo to give the title compound, nmr (CDCl$_3$) δ 2.21 (s, 3H), 3.37+4.0 (ABq, J=16 Hz, 2H), 4.47 (s, 2H), 4.52 (d, J=4 Hz, 1H), 5.23 (s, 2H), 5.35 (dd, J=4 and 8 Hz, 1H), 6.6-8.2 (m, 10H).

EXAMPLE 15 p-Nitrobenzyl 7-(phenoxyacetamido)desacetoxycephalosporanate 1α-oxide

To a stirred suspension of p-nitrobenzyl 7-aminodesacetoxycephalosporanate 1α-oxide hydrochloride (1.0 g) in methylene chloride (25 ml) at 0° C. was added a solution of sodium bicarbonate (0.462 g) in water (10 ml) followed by dropwise addition of phenoxyacetyl chloride (0.38 ml). After stirring the reaction mixture for one hour at 0°-5°, the organic layer was separated, washed with water and then with brine, dried with magnesium sulphate and evaporated under reduced pressure to give a yellow foam which on trituration with diethyl ether gave the title compound as white crystals.

The following compounds were prepared in a similar manner:

Benzhydryl 7-(phenoxyacetamido)desacetoxycephalosporanate 1α-oxide, white crystals, nmr (CDCl$_3$) δ 2.13 (s, 3H), 3.17+3.79 (ABq, J=16 Hz, 2H), 4.3-4.5 (m, 3H), 5.28 (dd, J=4 and 7.5 Hz, 1H), 6.6-7.4 (m, 16H), 7.69 (d, J=7.5 Hz, 1H).

p-Methoxybenzyl 7-(phenoxyacetamido)desacetoxycephalosporanate 1α-oxide, nmr (CDCl$_3$) δ 2.0 (s, 3H), 3.17+3.77 (ABq, J=17 Hz, 2H), 3.58 (s, 3H), 4.32 (m, 3H), 4.97 (s, 2H), 5.24 (dd, J=4 and 8 Hz, 2H), 6.5-7.2 (m, 9H), 7.87 (d, J=8 Hz, 1H).

EXAMPLE 16 p-Nitrobenzyl 3-chloro-7-(2,2,5,5-tetramethyl-1-aza-2,5-disilacyclopent-1-yl)-3-cephem-4-carboxylate A solution of 1,2-bis(chlorodimethylsilyl)ethane (3.2 g) in methylene chloride (20 ml) was added to a stirred mixture of p-nitrobenzyl 7-amino-3-chloro-3-cephem-4-carboxylate (5.0 g) and triethylamine (4.9 ml) in methylene chloride (25 ml) under a nitrogen atmosphere. The mixture was stirred at reflux for 16 hours, then allowed to cool to room temperature, and washed with 8% aqueous sodium hydrogen phosphate solution. The organic layer was separated, dried with magnesium sulphate, and evaporated under reduced pressure to give the title compound as a gum, nmr (CDCl$_3$) δ 0.17 (s, 12H), 0.78 (s, 4H), 3.38+3.82 (ABq, J=18 Hz, 2H), 4.76 (d, J=4 Hz, 1H), 4.93 (d, J=4 Hz, 1H), 5.28 (s, 2H), 7.3-8.1 (m, 4H).

EXAMPLE 17 p-Nitrobenzyl 3-chloro-7-(2,2,5,5-tetramethyl-1-aza-2,5-disilacyclopent-1-yl)-3-cephem-4-carboxylate 1α-oxide 36% Peracetic acid (2.25 ml) was added dropwise to a rapidly stirred mixture of saturated aqueous sodium bicarbonate (60 ml) and a solution of p-nitrobenzyl 3-chloro-7-(2,2,5,5-tetramethyl-1-aza-2,5-disilacyclopent-1-yl)-3-cephem-4-carboxylate (6.57 g) in methylene chloride (30 ml) at 0°-5° C. The mixture was stirred for 30 minutes at 0°-5° C. and then the organic layer was separated, washed with water, dried with magnesium sulphate, and evaporated to give the title compound as a yellow foam, nmr (CDCl$_3$) δ 0.15 (s, 6H), 0.24 (s, 6H), 0.80 (s, 4H), 3.56+4.22 (ABq, J=18 Hz, 2H), 4.43 (d, J=4 Hz, 1H), 5.10 (d, J=4 Hz, 1H), 5.30 (s, 3H), 7.3-8.1 (m, 4H).

EXAMPLE 18 p-Nitrobenzyl 3-chloro-7-(phenoxyacetamido)-3-cephem-4-carboxylate 1α-oxide

Phenoxyacetyl chloride (0.81 ml) was added to a stirred solution of p-nitrobenzyl 3-chloro-7-(2,2,5,5-tetramethyl-1-aza-2,5-disilacyclopent-1-yl)-3-cephem-4-carboxylate 1α-oxide (2.80 g) in tetrahydrofuran (85 ml) at room temperature. The mixture was stirred for one hour at room temperature, washed with saturated aqueous sodium bicarbonate and then water, dried with magnesium sulphate, and evaporated under reduced pressure to give a gum which was crystallised from isopropanol. The product was isolated by filtration, washed with isopropanol and then dried in vacuo to give the title compound as white crystals, nmr (CDCl$_3$) δ 3.75+4.45 (ABq, J=18Z, 2H), 4.5 (s, 2H), 4.74 (d, J=4 Hz, 1H), 5.52 (dd, J=4 and 8 Hz, 1H), 6.6-8.2 (m, 10H).

EXAMPLE 19

2,2,2-Trichloroethyl 7-(phenoxyacetamido)desacetoxycephalosporanate 1α-oxide A solution of phenoxyacetyl chloride (0.15 ml) and 2,2,2-trichloroethyl 7-(2,2,5,5-tetramethyl-1-aza-2,5-disilacyclopent-1-yl)desacetoxycephalosporanate 1α-oxide (0.5 g) in tetrahydrofuran (15 ml) was stirred for one hour at room temperature, washed with saturated aqueous sodium hydrogen carbonate and then water, dried with magnesium sulphate and evaporated to give an oil which was crystallised from di-isopropyl ether to give the title compound as white crystals, nmr (CDCl$_3$) δ 2.26 (s, 3H), 3.36+4.01 (ABq, J=18 Hz, 2H), 4.3–4.5 (m, 3H), 4.78 (s, 2H), 5.25 (dd, J=4 and 8 Hz, 1H), 6.4–7.3 (m, 5H), 7.60 (d, J=8 Hz, 1H).

We claim:

1. A process for preparing a compound of the formula

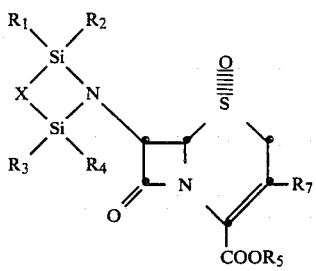

which comprises combining a cephem compound of the formula:

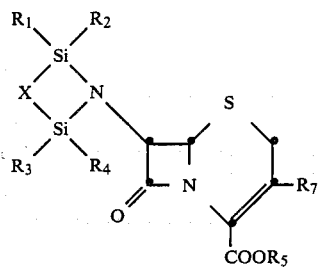

with a peracid oxidising agent and a sufficient amount of base so as to maintain the pH of the process from between about seven to about thirteen; and wherein:

$R_1$, $R_2$, $R_3$ and $R_4$ are the same or different and are chosen from the group consisting of $C_1$ to $C_4$ alkyl, $C_1$ to $C_4$ alkoxy, phenyl, and phenyl substituted with from one to three $C_1$ to $C_4$ alkyl, nitro, halo and $C_1$ to $C_4$ alkoxy groups, $R_7$ is methyl, halo, halomethyl or acetoxymethyl; and X is an alkylene group of the formula:

$$-(CH_2)_n-$$

wherein n is an integer from one through five.

2. A process of claim 1, which comprises combining the cephem compound with a peracid oxidising agent and a sufficient amount of base so as to maintain the pH of the process between about eight to about eleven; and wherein:

$R_1$, $R_2$, $R_3$ and $R_4$ are the same or different and are $C_1$ to $C_4$ alkyl;

$R_5$ is benzhydryl, para-nitrobenzyl, para-methoxybenzyl or 2,2,2-trichloroethyl;

$R_7$ is chloro or methyl;

n is two; and the oxidizing agent is meta-chloroperbenzoic acid, peracetic acid or monoperphthalic acid.

* * * * *